United States Patent [19]

Camacho

[11] Patent Number: 5,445,723
[45] Date of Patent: Aug. 29, 1995

[54] BLOTTING APPARATUS

[75] Inventor: Joseph Camacho, San Francisco, Calif.

[73] Assignee: Hoefer Scientific Instruments, San Francisco, Calif.

[21] Appl. No.: 252,571

[22] Filed: May 31, 1994

[51] Int. Cl.⁶ ............................................. G01N 27/28
[52] U.S. Cl. ............................. 204/299 R; 204/300 R
[58] Field of Search ................. 204/180.1, 286, 299 R

[56] References Cited

U.S. PATENT DOCUMENTS

| | | | |
|---|---|---|---|
| 4,589,965 | 5/1986 | Kreisher | 204/182.8 |
| 4,913,791 | 4/1990 | Hurd et al. | 204/299 R |
| 5,100,525 | 3/1992 | Pohto et al. | 204/280 |
| 5,217,592 | 6/1993 | Jones | 204/299 R |

Primary Examiner—John Niebling
Assistant Examiner—Shou Hwa Yeah
Attorney, Agent, or Firm—Limbach & Limbach; W. Patrick Bengtsson

[57] ABSTRACT

A blotting apparatus for transferring electrophoretically separated material from electrophoresis gels in a transfer stack. The device includes a resilient anode surface for more consistent transfer of DNA from DNA sequencing gels in the transfer stack to an immobilizing membrane. The anode surface is smaller than the cathode surface, and is mounted on a carrier arm which moves the anode surface over the membrane during transfer.

12 Claims, 4 Drawing Sheets

BLOTTING APPARATUS

FIELD OF THE INVENTION

This invention relates to a device for electrophoretically transferring biological molecules from electrophoresis gels, and in particular to a blotting apparatus particularly useful for transferring DNA from DNA sequencing gels to an immobilizing membrane using a resilient anode.

BACKGROUND OF THE INVENTION

Electrophoresis gels are useful for the separation of biological molecules including proteins, RNA, DNA and carbohydrates. The transfer of electrophoretically separated material by blotting has become a standard procedure for sensitive and specific analysis of electrophoresis gels.

Early blotting techniques involved the use of capillary action to transfer material from electrophoresis gels. These techniques were slow and inefficient requiring up to 16 hours or more to transfer all of the material from a gel.

Blotting under the influence of an electric field offers significant advantages over capillary transfer techniques. In particular, such blotting is generally quicker and more efficient than capillary transfer. Capillary transfer and blotting using an electric field both require that a gel be placed in contact with an immobilizing-membrane to which the electrophoretically separated biological molecules are transferred. This combination is sometimes referred to as a "transfer stack." The stack usually also includes one or more sheets of buffer-wetted filter paper sheets on both the top and bottom of the stack for ease of handling and to protect fragile membranes from contamination or damage. In capillary transfer the transfer force is the absorptive potential of the immobilizing transfer membrane and, usually, additional dry (bibulous or highly absorptive) paper on the opposing side of the membrane. In blotting using an electric field, the driving force is the electrode potential between the two electrodes placed on either side of the transfer stack.

Although more efficient than capillary blotting, electric blotting techniques can also suffer from significant disadvantages. These disadvantages include: non-uniform electric fields at the transfer stack surfaces and voltage leakage around the surfaces of the electrodes both which result in inefficient or inconsistent transfer of DNA.

One prior art solution (U.S. Pat. No. 4,589,965) involves sandwiching a gel/immobilizing transfer material between two electrodes of equal size. Although this method was more efficient than previous techniques, it still suffered from inconsistent transfer problems. Gel/-transfer material "sandwich" surfaces (i.e. blotting membrane surfaces) are inherently uneven. As a result, it is difficult to obtain consistent contact between the electrode surface and the blotting membrane. Accurate transfer across the entire gel is critical for subsequent analyses of the blotted macromolecules.

Another disadvantage of prior blotting apparatus is the cost of the relatively large surface area electrodes, in part due to the use of platinum on the electrodes. One solution to this problem is found in the GeneSweep TM brand blotting apparatus sold by Hoefer Scientific Instruments of San Francisco, Calif., assignee of the present application. In the GeneSweep TM device, one of the electrodes is made smaller than the opposing electrode, but movable along the upper surface of the blotting membrane. However, this device still suffers from a lack of consistent contact between the electrode surface and the blotting membrane.

It would therefore be advantageous to have a device which would transfer electrophoretically separated material rapidly, reproducibly and uniformly, yet avoid the drawbacks of prior systems.

SUMMARY OF THE INVENTION

In order to address these concerns, the present invention provides a blotting apparatus for transferring electrophoretically separated material from electrophoresis gels which apparatus includes a resilient electrode surface structure. The resilience of the electrode structure provides for improved contact across the entire electrophoretic transfer surface area.

Thus, in a first embodiment, the invention is directed to a blotting apparatus including a base, a cathode having a first surface area mounted on the base, a carrier arm movably mounted along a length of the base, an anode having a second surface area which is smaller than the first surface area and which is mounted on the carrier arm and facing the cathode, and means for permitting resilient movement of portions of the anode.

In a second embodiment, the blotting apparatus comprises a cathode having a first surface area, an anode having a second surface area smaller than said first surface area, arm .means for moving the second surface over the first surface, wherein the second surface is resiliently mounted on the arm means.

The present invention is also directed to a method for rapid molecular transfer from a gelatinous sheet to a transfer membrane comprising the steps of providing an electrophoretically resolved material in a gelatinous sheet, placing the gelatinous sheet on a first electrode surface, positioning a transfer membrane over the gelatinous sheet, contacting a resilient surface of a second electrode with a surface of said membrane, applying an electric potential across said first and second electrodes, and transferring the electrophoretically resolved material to the membrane by moving the second electrode along the surface of the membrane.

BRIEF DESCRIPTION OF THE DRAWINGS

The invention will be better understood by reference to the appended drawings of which.

DETAILED DESCRIPTION OF THE INVENTION

The present invention provides an effective structure for transferring electrophoretically separated material rapidly, reproducibly and uniformly to an immobilizing membrane, a process generally referred to in the art as blotting.

A key feature of the invention is the use of a resilient anode surface which surface is placed in contact (usually through a sheet of buffer-wetted filter paper) with the membrane to which the desired materials will be electrophoretically transferred. By "resilient" it is meant that a surface is flexible in and of itself, or is flexibly mounted, so that the surface tends to conform to another surface (the membrane or "the membrane side of the transfer stack" since it may be protected with paper) with which the resilient surface is in contact, thus improving the uniformity of the electric field across the transfer stack.

Figure 1:
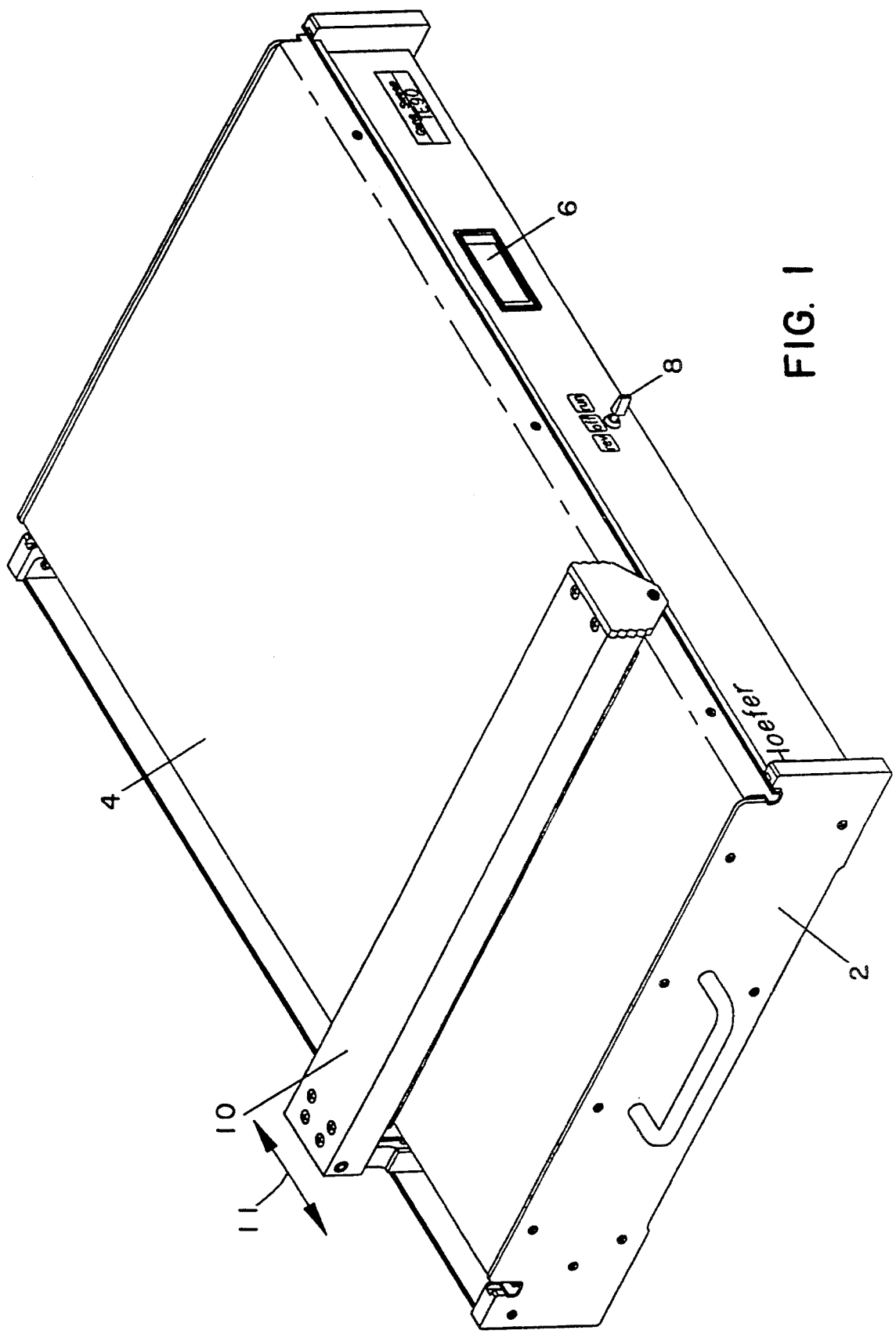
FIG. 1 is a perspective view of a preferred embodiment of the invention.

FIG. 1 is a perspective view of the exterior of the electrophoretic transfer instrument which incorporates the invention. The instrument includes a cabinet 2 which surrounds and supports a flat transfer platform 4. The upper surface of platform 4 becomes the cathode during operation. Also shown in FIG. 1 is panel meter 6 which displays the current running through the transfer stack (not shown) during operation. Function switch 8 is used to activate the apparatus and has a "run" position in which arm assembly 10 moves along an edge of cabinet 2 as indicated by arrow 11. A "reverse" position for the switch is used to reset the apparatus by moving arm 10 to its original position. During operation arm assembly 10 (carrying the anode) will travel along the length of base 2 at approximately 5 cm per minute. A voltage of 30 volts is typical. The amperage may vary, but will normally range between 1 and 2 amps. The device is designed so that the blotting voltage is automatically turned off when arm 10 reaches the end of platform 4. The reverse speed of 60 cm per minute is designed to permit quick reset of the arm.

Figure 2:
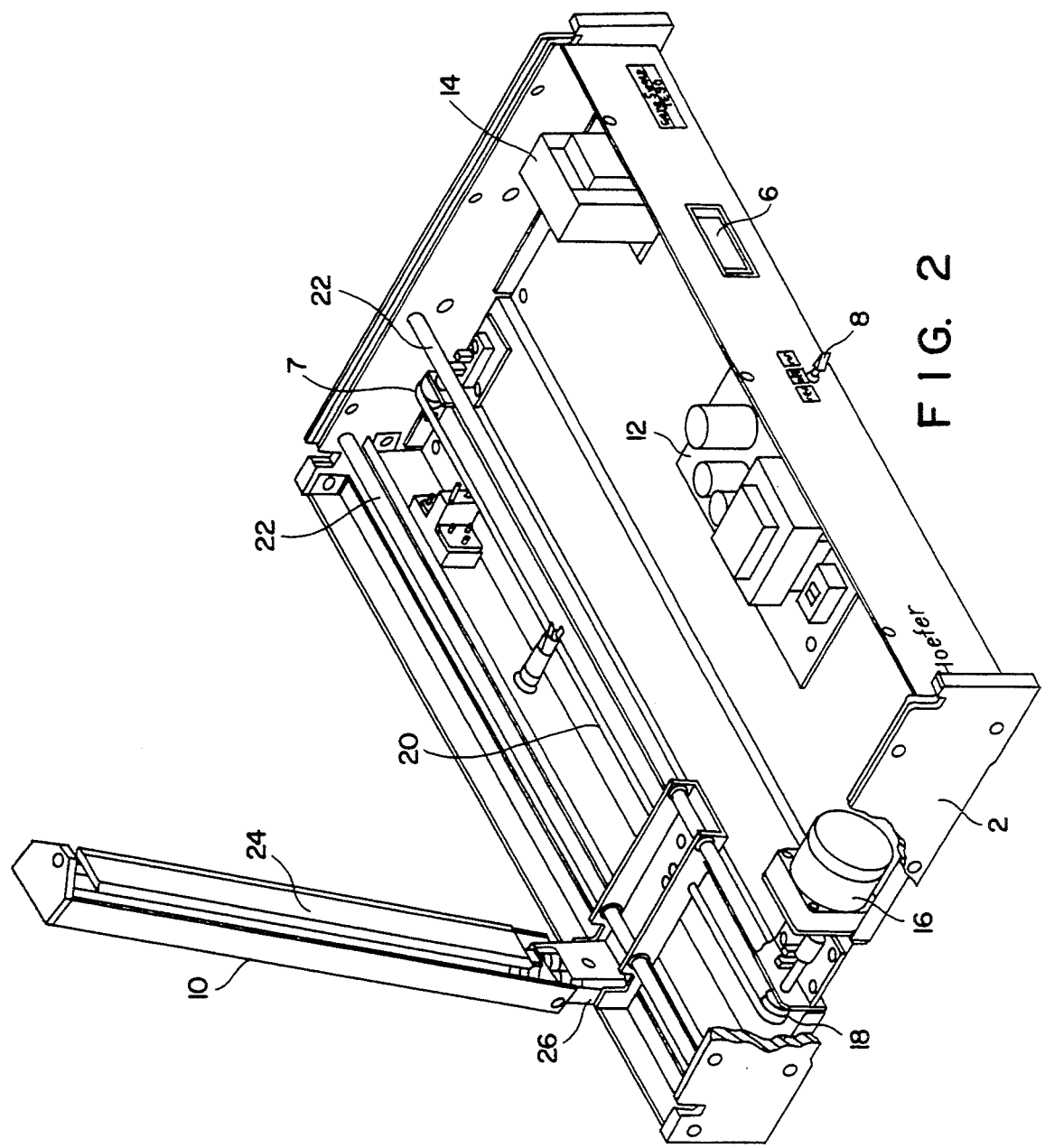
FIG. 2 is a perspective cut-away view of the components of the blotting apparatus of the invention.

FIG. 2 provides a perspective cut-away view of the blotting apparatus of the invention. The reference numerals used in FIG. 2 refer to the same elements of the apparatus as those shown in FIG. 1, as well as FIGS. 3 and 4. In FIG. 2, arm assembly 10 is shown in its raised position (exposing anode assembly 24), which position is used when blotting material (the transfer stack) is being positioned over platform 4. As can be seen, cabinet 2 houses electronics 12, a transformer 14 and a motor 16 which drives arm assembly 10 along the length of the apparatus. When activated, motor 16 causes drive pulley 18 to move belt 20, and with it arm 10, along guide rails 22. An idler pulley 7 provides support and tension adjustment for belt 20. A 12 volt stepper motor is preferably used. The drive belt is a one quarter inch wide 3.9 foot long band.

Figure 3:
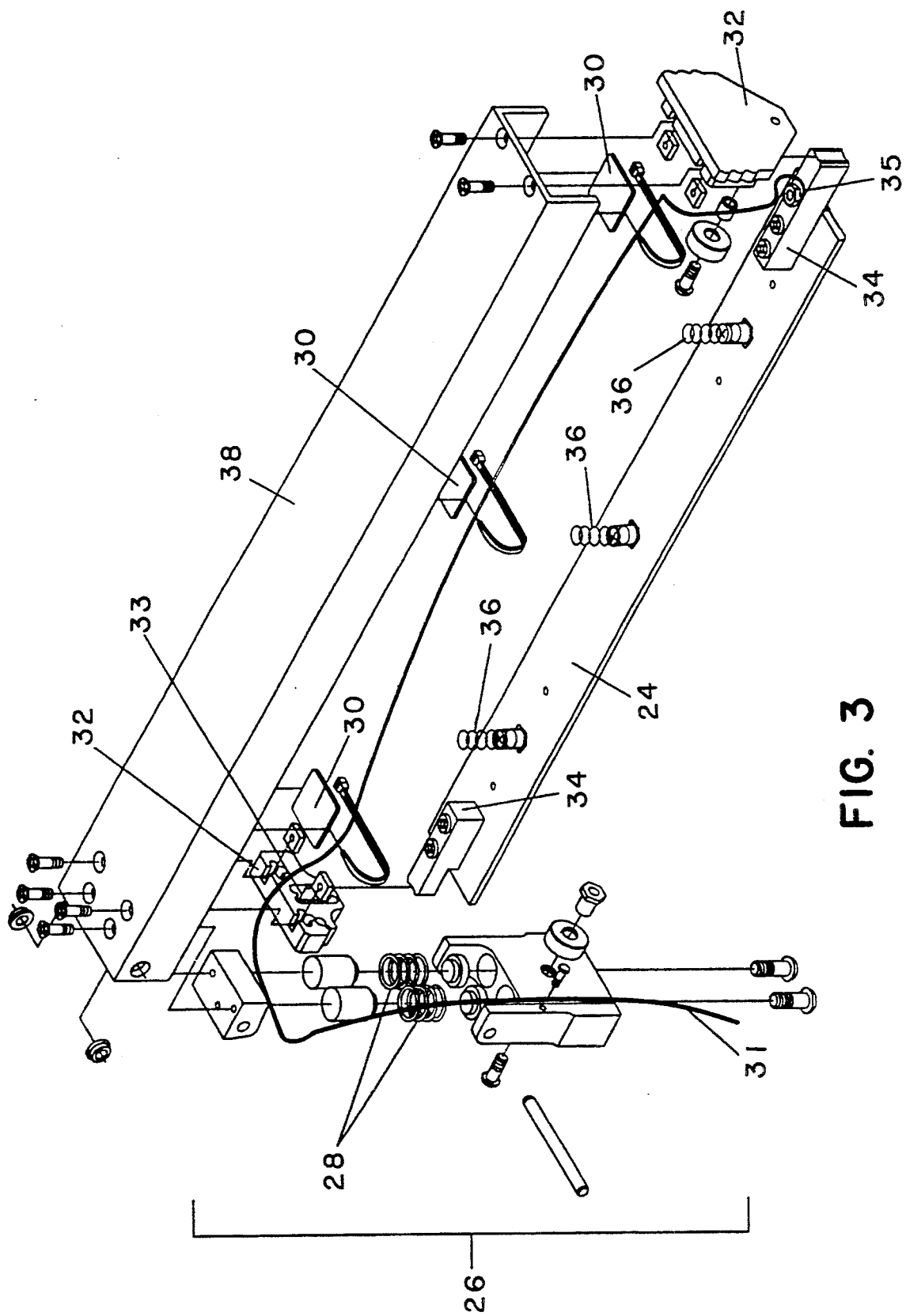
FIG. 3 is an exploded perspective view of the components of the arm and anode of the preferred embodiment.
Figure 4:
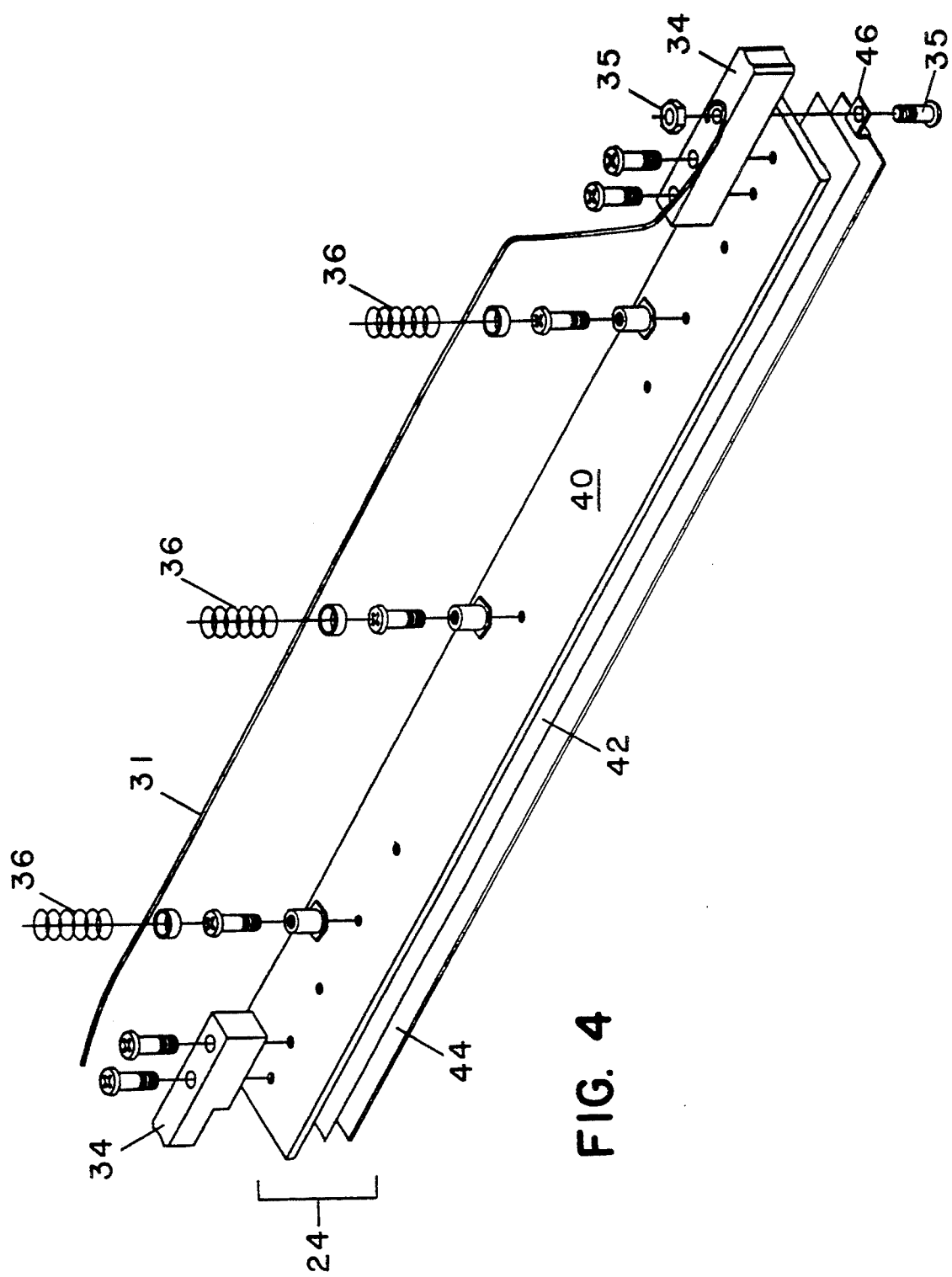
FIG. 4 is an exploded perspective view of the components of the resilient anode structure of the preferred embodiment.

The resilient anode feature of the invention is highlighted in FIGS. 3 and 4. In FIG. 3, arm assembly 10 is shown in an exploded view. Arm mounting assembly 26 is used to support arm assembly 10. In assembly 26, springs 28 are used to permit the raising and lowering of the arm between the loading position and the position of the arm during use. In its lowered position, arm assembly 10 supports the anode an appropriate distance above, and facing, the cathode surface, which distance remains constant as the arm assembly moves along the length of the cabinet. Power is carried to anode assembly 24 via wire 31 which is connected to electrode tab 46 by screw and nut 35. Wire hold downs 30 secure wire 31.

In this embodiment, anode assembly 24 is constrained to move only vertically and prevented from twisting by support arms 34 which ride in slots 33 in end supports 32. Springs 36 permit resilient vertical movement of the anode assembly relative to end support 32 as the arm moves along the length of cabinet 2.

Anode assembly 24 is shown in further detail in FIG. 4, and is constructed of three relatively thin layers 40, 42 and 44. The actual platinized niobium electrode layer 44 is approximately 2.5 cm by 33 cm by 0.05 cm and is electrically connected to the power supply of the apparatus via wire 31 through nut and screw 35 and electrode tab 46. The flexibility of the anode assembly 24 is determined by the material and design of layers 40 and 42. Layer 40 is made of acrylic plastic and layer 42 is double-faced adhesive tape. Layers 40 and 42 give the anode assembly adequate strength and stiffness required for day to day use while permitting the anode assembly to flex as variations in the surface of the transfer stack are reached as the anode passes from a first edge to the end edge of the stack. The platinized niobium electrode 44 is too flexible and prone to damage if unsupported, so an acrylic stiffener provides the required degree of control. Double-faced adhesive tape 42 provides a secure bond without affecting resilience significantly.

The flexible/resilient electrode design of the invention provides substantial performance benefits over the prior design of the GeneSweep TM apparatus. In the original version, an attempt was made to solve the problem of inconsistent contact by keeping both electrodes as flat as possible. In the original version, the lower large electrode was braced with spot welded cross struts on the underside, and the smaller anode was backed with a thick piece of acrylic. However, passing 2 amps through the transfer stack at 30 volts generated so much heat that, despite such bracing, the electrodes still bowed away from one another, reducing contact to a narrow band in the center at some points, further exacerbating the problem.

It will be understood that the flexibility provided by the resilient anode of the present invention takes a completely different approach, i.e. instead of finding new ways to brace the electrodes in a way would stiffen them and, hopefully, avoid loss of consistent contact, the present invention solves the problem by making the anode surface resilient. It will be understood by those skilled in the art that any design which permits the electrode surface or surfaces to "float" relative to the surface with which consistent contact is required is "resilient" within the meaning of the invention. The limits of such resilience occur in any design where the two electrodes cannot maintain a substantially uniform contact with the transfer stack under transfer heating stresses.

The electrical/control elements of the invention can be varied as desired and as is well known in the art, to deliver the desired anode/cathode performance characteristics. For completeness-sake, however, it is noted that the blotting power supply of the preferred embodiment will deliver approximately 30 volts and up to 2 amps to the anode arm. Electronics 12 provides, in a manner well-known to those skilled in the art, the necessary conversion from AC line voltage to 30 volts DC, output voltage and current regulation and control and regulates AC line voltage to $+15$ volts DC, $-5$ volts DC and $+5$ volts DC conversion for the power supply control electronics. Transformer 14 acts as an output power transformer.

The apparatus of the invention can be used to electrically blot large gels such as sequencing and large electrophoresis gels. The small size of the anode minimizes the cost of platinum which would otherwise be required. Further, the resiliency of the anode permits improved contact between the anode and gel stack so that more consistent results are achieved.

Although only the most preferred embodiment of the invention has been shown and described, many modifications and rearrangements which nevertheless incorporate the important features of the invention will be readily apparent to those skilled in the art of blotting by application of electric fields. For example, many differently shaped resilient anode (or even cathode) structures can be imagined; a segmented conductive brush electrode for one, or a closely spaced array of conductive washers loosely suspended on a conductive rod, for a second. Numerous methods could be used which would still minimize the active resilient surface area and move that surface over the transfer stack by varying the shape of that surface and/or moving the active anode surface in directions other than simply along the length of the base (e.g. a clock-like arrangement having circular cathode with the anode sweeping over the surface of the cathode like the hands of a clock). Such modifications are considered to be within the scope of the appended claims.

What is claimed is:

1. A blotting apparatus comprising:
   a first electrode;
   a carrier arm;
   a second electrode resiliently mounted on said arm wherein said first electrode has a first surface area, and said second electrode is spaced from and facing said first electrode and said second electrode has a second surface area which is smaller than said first surface area.

2. A blotting apparatus as in claim 1 wherein said arm is movable along a length of said first electrode.

3. A blotting apparatus as in claim 2 wherein said first electrode is a cathode and said second electrode is an anode.

4. A blotting apparatus comprising:
   a base electrode, said base electrode having a first surface area;
   an upper electrode, said upper electrode having a second surface area smaller than said first surface area;
   arm means for passing said second surface over said first surface, wherein said second electrode surface is resiliently mounted on said arm means.

5. A blotting apparatus as in claim 4 wherein said second electrode surface is spring mounted on said arm.

6. A blotting apparatus as in claim 5 wherein said first electrode is a cathode and said second electrode is an anode.

7. A blotting apparatus comprising:
   first electrode means adapted to act as a blotting electrode means;
   a carrier arm positioned adjacent said first electrode means and movable along a length thereof;
   a second electrode resiliently mounted on said arm, wherein said second electrode is spaced from and facing said blotting electrode means.

8. A blotting apparatus as in claim 7, wherein said arm is movable from a first position in which said second electrode is in contact with a gelatinous sheet when said sheet is positioned on said blotting electrode means, to a second position in which said second electrode is no longer in contact with said gelatinous sheet when said sheet is positioned on said blotting electrode means.

9. A blotting apparatus comprising:
   a first electrode including a rectangular face having a first surface area for supporting a gelatinous sheet;
   a carrier arm positioned adjacent said first electrode, said carrier arm being movable along a length of said first electrode;
   a second electrode mounted on said arm and including a rectangular face, said second electrode rectangular face being spaced from and facing said first electrode face and having a second surface area which is smaller than said first surface area;
   springs resiliently connecting said arm and said second electrode.

10. A blotting apparatus as in claim 9 further comprising a layer of plastic mounted on a surface of said second electrode for providing stiffness to said electrode.

11. A blotting apparatus as in claim 9 wherein said second electrode is platinized niobium.

12. A blotting apparatus as in claim 9 wherein springs are coil springs.

* * * * *